US009206425B2

(12) United States Patent
Chang et al.

(10) Patent No.: US 9,206,425 B2
(45) Date of Patent: Dec. 8, 2015

(54) METHODS FOR TREATING NIEMANN-PICK TYPE C DISEASE

(75) Inventors: Ta-Yuan Chang, Etna, NH (US); Catherine C. Y. Chang, Etna, NH (US); Maximillian A. Rogers, White River Junction, VT (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 14/235,482

(22) PCT Filed: Jul. 24, 2012

(86) PCT No.: PCT/US2012/047927
§ 371 (c)(1),
(2), (4) Date: Mar. 26, 2014

(87) PCT Pub. No.: WO2013/016315
PCT Pub. Date: Jan. 31, 2013

(65) Prior Publication Data
US 2014/0220114 A1 Aug. 7, 2014

Related U.S. Application Data

(60) Provisional application No. 61/512,615, filed on Jul. 28, 2011.

(51) Int. Cl.
*C12N 15/11* (2006.01)
*C12N 15/113* (2010.01)
*A61K 31/7105* (2006.01)
*A61K 31/713* (2006.01)

(52) U.S. Cl.
CPC ............ *C12N 15/113* (2013.01); *A61K 31/713* (2013.01); *A61K 31/7105* (2013.01); *C12N 15/1137* (2013.01); *C12Y 203/01009* (2013.01); *C12N 2310/14* (2013.01); *C12N 2310/141* (2013.01)

(58) Field of Classification Search
CPC ............................ C12N 15/113; A61K 31/713
See application file for complete search history.

(56) References Cited

U.S. PATENT DOCUMENTS

| 7,560,449 | B2 | 7/2009 | Fine et al. .................. 514/183 |
| 2005/0118226 | A1 | 6/2005 | Kovacs et al. .............. 424/423 |
| 2006/0257466 | A1 | 11/2006 | Kim et al. .................. 424/450 |
| 2011/0237656 | A1 | 9/2011 | Chang et al. ............... 514/44 R |

FOREIGN PATENT DOCUMENTS

WO    WO 2010042292 A1 *  4/2010

OTHER PUBLICATIONS

International Preliminary Report on Patentability from PCT/US2012/047927, Feb. 6, 2014.

Bryleva et al. "ACAT1 Gene Ablation Increases 24(S)-Hydroxycholesterol Content in the Brain and Ameliorates Amyloid Pathology in Mice with AD" Proceedings of the National Academy of Sciences 2010 107(7):3081-3086.
Chang et al. "Acyl-Coenzyme A: Cholesterol Acyltranferases" American Journal of Physiology, Endocrinology, and Metabolism 2009 297:E1-E9.
Davidson et al. "Chronic Cyclodextrin Treatment of Murine Niemann-Pick C Disease Ameliorates Neuronal Cholesterol and Glycosphingolipid Storage and Disease Progression" PLoS ONE 2009 4(9):e6951.
Dove et al. "ACAT1 Deficiency Disrupts Cholesterol Efflux and Alters Cellular Morphology in Macrophages" Arteriosclerosis, Thrombosis, and Vascular Biology 2005 25:128-134.
German et al. "Degeneration of Neurons and Glia in the Niemann-Pick C Mouse Is Unrelated to the Low-Density Lipoprotein Receptor" Neuroscience 2001 105(4):999-1005.
Ikenoya et al. "A Selective ACAT-1 Inhibitor, K-604, Suppresses Fatty Streak Lesions in Fat-Fed Hamsters Without Affecting Plasma Cholesterol Levels" Atherosclerosis 2007 191(2):290-297.
Kaptzan et al. "Development of a Rab9 Transgenic Mouse and its Ability to Increase the Lifespan of a Murine Model of Niemann-Pick Type C Disease" The American Journal of Pathology 2009 174(1):14-20.
Li et al. "GM2/GD2 and GM3 Gangliosides Have No Effect on Cellular Cholesterol Pools or Turnover in Normal or NCP1 Mice" Journal of Lipid Research 2008 49:1816-1828.
Liu et al. "Cyclodextrin Overcomes the Transport Defect in Nearly Every Organ of NPC1 Mice Leading to Excretion of Sequestered Cholesterol as Bile Acid" Journal of Lipid Research 2010 51:933-944.
Liu et al. "Genetic Variations and Treatments that Affect the Lifespan of the NPC1 Mouse" Journal of Lipid Research 2008 49:663-669.
Loftus et al. "Murine Model of Niemann-Pick C Disease: Mutation in a Cholesterol Homeostasis Gene" Science 1997 277:232-235.
Masciullo et al. "Substrate Reduction Therapy with Miglustat in Chronic GM2 Gangliosidosis Type Sandhoff: Results of a 3-Year Follow-Up" Journal of Inherited Metabolic Disease 2010 33(Suppl 3):S355-S361.
Patterson et al. "Long-Term Miglustat Therapy in Children with Niemann-Pick Disease Type C" Journal of Child Neurology 2010 25(3):300-305.
Quan et al. "Ontogenesis and Regulation of Cholesterol Metabolism in the Central Nervous System of the Mouse" Developmental Brain Research 2003 146:87-98.
Ramirez et al. "Weekly Cyclodextrin Administration Normalizes Cholesterol Metabolism in Nearly Every Organ of the Niemann-Pick Type C1 Mouse and Markedly Prolongs Life" Pediatric Research 2010 68(4):309-315.
Reid et al. "A Novel Cholesterol Stain Reveals Early Neuronal Cholesterol Accumulation in the Niemann-Pick Type C1 Mouse Brain" Journal of Lipid Research 2004 45:582-591.

(Continued)

*Primary Examiner* — J. E. Angell
(74) *Attorney, Agent, or Firm* — Licata & Tyrrell P.C.

(57) ABSTRACT

The present invention includes methods for treating Niemann-Pick Type C disease through administration of inhibitors of acyl-coenzyme A:cholesterol acyltransferase 1 (ACAT1). ACAT inhibitors are used to treat symptoms of Niemann-Pick Type C disease and prolong survival of patients with the disease, either alone or in combination with other treatments.

5 Claims, 1 Drawing Sheet

(56) References Cited

OTHER PUBLICATIONS

Repa et al. "Liver X Receptor Activation Enhances Cholesterol Loss from the Brain, Decreases Neuroinflammation, and Increases Survival of the NPC1 Mouse" the Journal of Neuroscience 2007 27(52):14470-14480.

Shapiro et al. "Miglustat in Late-Onset Tay-Sachs Disease: A 12-Month, Randomized, Controlled Clinical Study with 24 Months of Extended Treatment" Genetics in Medicine 2009 11(6):425-433.

Tallaksen, C.M.E. and Berg, J.E. "Miglustat Therapy in Juvenile Sandhoff Disease" Journal of Inherited Metabolic Disease 2009 32(Suppl 1):S289-S293.

Wraith, J.E. and Imrie, J. "New Therapies in the Management of Niemann-Pick Type C Disease: Clinical Utility of Miglustat" Therapeutics and Clinical Risk Management 2009 5:877-887.

International Search Report from PCT/US2012/047927, Oct. 16, 2012.

\* cited by examiner

METHODS FOR TREATING NIEMANN-PICK TYPE C DISEASE

INTRODUCTION

This application is a U.S. National Stage Application under 35 U.S.C. §371 of PCT International Application No. PCT/US2012/047927, filed Jul. 24, 2012, which claims the benefit of priority of U.S. Provisional Application Nos. 61/512,615, filed Jul. 28, 2011, the contents of each of which are incorporated herein by reference in their entirety.

This invention was made with government support under R01AG037609 and R01HL036704 awarded by the National Institutes of Health. The government has certain rights in the invention.

BACKGROUND OF THE INVENTION

Niemann-Pick Type C (NPC) disease is a rare, pediatric, genetically recessive neurological disease. NPC is caused by mutations in genes known as either Npc1, which encodes a membrane protein with 13-16 transmembrane domains (TMD), or, in approximately 5% of patients, Npc2, which encodes a soluble protein. Loss of function in either the NPC1 or NPC2 protein results in clinically indistinguishable disease phenotypes, with accumulation of cholesterol, sphingomyelin, sphingosine, and gangliosides GM2 and GM3 within the late endosomes/lysosomes. This accumulation of lipids results in progressive neurodegeneration, hepatomegaly and splenomegaly, and ultimately early death, usually before age 20 years. Currently, this disease has no cure.

NPC1 and NPC2 are endosomal cholesterol binding proteins that work in concert to transport cholesterol out of the late endosomes/lysosomes to various cellular compartments, including the endoplasmic reticulum (ER). Acyl-coenzyme A:cholesterol acyltransferase 1 (ACAT1) is a resident enzyme located at the ER that utilizes cholesterol and fatty acyl-coenzyme A as its substrates to produce cholesteryl esters. ACAT1 is responsible for the bulk of cellular cholesteryl esters found in various cells. Lacking functional NPC1 or NPC2 considerably slows the transport rate of cholesterol from the late endosomes/lysosomes to the ER. However, through NPC1/NPC2-independent mechanisms for delivering cholesterol, enough cholesterol eventually arrives at the ER for esterification. Thus, a significant amount of cholesteryl ester is still present in mutant NPC cells.

Several mouse models for NPC disease are available. In the original NPC1$^{-/-}$ mice, alteration within the Npc1 gene causes a frame-shift mutation and results in premature truncation of the NPC1 protein (Loftus et al. 1997. Science 277: 232-235). Neuronal cholesterol accumulation occurs as early as postnatal day (PND) 9 in the mouse model (Reid et al. 2004. J. Lipid Res. 45:582-591), then loss of Purkinje neurons in the cerebellum begins to occur shortly after weaning (at PND 21) (German et al. 2001. Neuroscience 105:999-1005). The mice begin to lose weight at 7 weeks of age, and begin to die at 11 weeks of age. In a newly discovered mutant NPC mouse model (the npc1$^{NMF164}$ mouse, also referred to as the Npc1$^{m/m}$ mouse), a point mutation occurs within the coding region of NPC1 (at D1005G). This mouse was discovered at the Jackson Laboratory as a result of chemically-induced mutagenesis. A noncomplementation test with other Npc1 alleles showed that NMF164 represents an allele of Npc1. The D1005G mutation is within the cysteine-rich luminal loop, where most common human mutations are found. In Npc1$^{m/m}$ mice, the npc1 mRNA levels appear relatively normal. Biochemical and histological analyses of liver, spleen, hippocampus, cortex, and cerebellum reveal abnormal cholesterol and glycolipid accumulation, glial activation, and progressive Purkinje cell loss. These mice exhibit characteristic gait and motor abnormalities, begin to lose weight at 8 weeks of age, and begin to die at 13 weeks of age; abnormalities very similar to the original NPC1$^{-/-}$ mouse. This model provides another useful tool for examining the pathogenesis of NPC disease as well as a model for testing potential new drug therapies.

Many different drug therapies have been attempted in order to treat NPC disease in efforts to either cure disease or to prolong the life of affected individuals. In mouse models for NPC disease, two drugs have shown promise. The first is Miglustat, also called NB-DNJ. Miglustat is an inhibitor of glycosphingolipid biosynthesis that reduces levels of all glucosylceramide-derived glycosphingolipids (GSLs) (Wraith and Imrie. 2009. Ther. Clin. Risk Manag. 5:877-887). Miglustat has shown efficacy in mouse models of GSL storage diseases, including Tay-Sachs and Sandhoff disease (Shapiro et al. 2009. Genet. Med. 11:425-433; Masciullo et al. 2010. J. Inherit. Metab. Dis. PMID: 20821051; Tallaksen and Berg. 2009. J. Inherit. Metab. Dis. PMID: 19898953). In cells affected by NPC disease, gangliosides, mostly GM2 and GM3, and neutral GSLs accumulate along with cholesterol within the late endosomes/lysosomes. When tested in the NPC1$^{-/-}$ mice, continuous administration of Miglustat starting at PND 7 significantly delayed the clinical onset and prolonged the lifespan by 49% (Davidson et al. 2009. PLoS One 4:e6951). In humans, a two-year study showed that Miglustat treatment stabilized NPC disease progression in 80% of patients (Patterson et al. 2009. J. Child Neurol. 25:300-305). Another drug that has shown some efficacy in animal models with NPC disease is hydroxypropyl beta-cyclodextrin (HPCD), a soluble cholesterol binder. HPCD can enter the cell interior and mobilize a portion of the cholesterol pool sequestered within the late endosomes/lysosomes in NPC cells. Single injection of HPCD to NPC1$^{-/-}$ mice at PND 7 prolonged their lifespan by 27% (Liu et al. 2009. J. Lipid Res. 51:933-944). Weekly treatment with HPCD was also shown to normalize cholesterol accumulation in NPC1$^{-/-}$ mice and to prolong survival (Ramirez et al. 2010. Pediatr. Res. 68:309-315). Problems associated with HPCD therapy include difficulty in crossing the blood brain barrier, and increases in macrophage activation in the lungs of treated NPC mice and NPC cats (Liu et al. 2009. J. Lipid Res. 51:933-944).

Other studies examining knockout of genes other than Acat1 gene that are involved in lipoprotein and cholesterol metabolism, such as Abca1, Apoa1, Apoe, Cyp46, Ldlr, Lxrβ, and SrbI, have not been associated with prolonged survival of NPC1$^{-/-}$ mice (Quan et al. 2003. Brain Res. Dev. Brain Res. 146:87-98; Repa et al. 2007. J. Neurosci. 27:14470-14480; Liu et al. 2008. J. Lipid Res. 49:663-669). Knockout of Siat9, a gene involved in biosynthesis of GM3 (Li et al. 2008. J. Lipid Res. 49:1816-1828), actually shortened the lifespan of NPC mice. Yet, over-expressing Rab9, a protein involved in membrane lipid trafficking, prolonged the lifespan of NPC1$^{-/-}$ mice by 22% (Kaptzan et al. 2009. Am. J. Pathol. 174:14-20).

As discussed above, acyl-CoA:Cholesterol Acyltransferase (ACAT) converts free cholesterol to cholesterol ester, and is a key enzymes in cellular cholesterol metabolism. While both ACAT1 and ACAT2 are present in the liver and intestine, the cells containing either enzyme within these tissues are distinct, suggesting that ACAT1 and ACAT2 have separate functions. As a result, both ACAT1 and ACAT2 are potential drug targets for treating diseases associated with cholesterol function, such as dyslipidemia and atherosclerosis. Dove et al. (2005. *Arterioscler. Thromb. Vasc. Biol.* 25:128-134) examined the role of ACAT1 deficiency on macrophage cholesterol efflux and cellular morphology. The authors were interested in understanding the mechanism for increased atherosclerosis in mouse models. They hypothesize that ACAT1$^{-/-}$ macrophages have a phenotype similar to NPC1$^{-/-}$ cells and that ACAT$^{-/-}$ increases intracellular vesicles that may release calcium stores and lead to apoptosis of the cells. Although inhibition of ACAT1 may be useful for treating a disease such as atherosclerosis, based on the findings of Dove et al. (2005. *Arterioscler. Thromb. Vasc. Biol.* 25:128-134), inhibition of ACAT1 in models of NPC disease would be expected to exacerbate the NPC phenotype and worsen disease.

It has now been found that contrary to predictions made in the art, inhibition of ACAT1 activity in NPC disease is an effective treatment that prolongs survival in animal models of NPC disease.

SUMMARY OF THE INVENTION

The present invention is a method for treating Niemann-Pick Type C (NPC) disease. The method of the invention includes administering to a patient diagnosed with NPC disease an effective amount of an ACAT inhibitor (e.g., having an IC$_{50}$ value in the range of 1 nM to 100 µM) in a pharmaceutically acceptable vehicle. In one embodiment, the ACAT inhibitor is administered in combination with one or more other drugs used to treat NPC disease. In some embodiments, the ACAT inhibitor inhibits both ACAT1 and ACAT2. In other embodiments, the ACAT inhibitor is a selective inhibitor of ACAT1, e.g., having an IC$_{50}$ value for ACAT1 which is at least twice the corresponding IC$_{50}$ value for ACAT2. In particular embodiments, the selective inhibitor of ACAT1 is an siRNA or microRNA, which can be administered via a liposome or nanoparticle.

DETAILED DESCRIPTION OF THE INVENTION

Figure 1A:
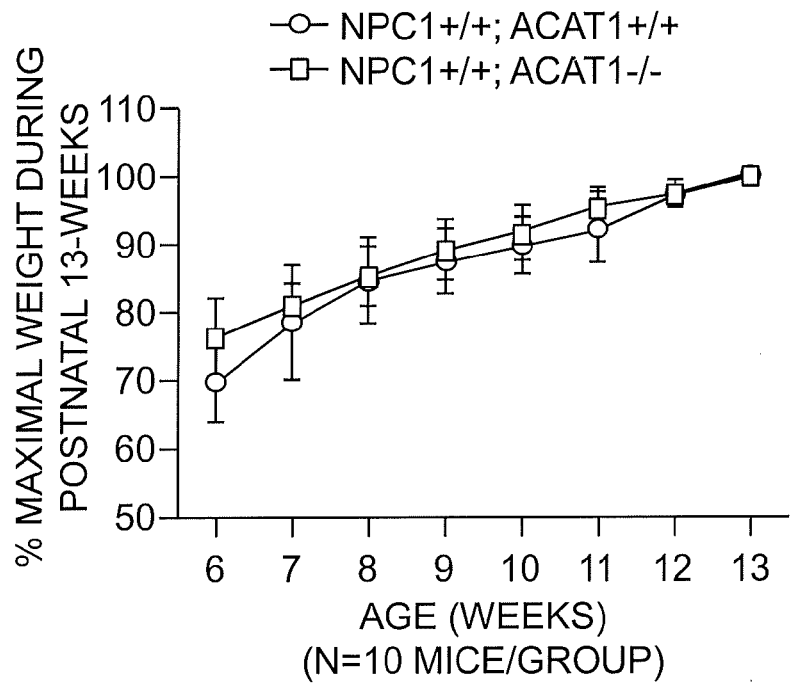
FIGS. 1A and 1B show that ACAT$^{-/-}$ delays weight loss of Npc1$^{m/m}$ mouse (FIG. 1A) without affecting weight of wild-type (Npc1$^{+/+}$) mice (FIG. 1B). Weight measurement began at 6 weeks of age. Data are expressed as percent of maximum weight during the first 13 weeks. N=10 mice per group with comparable numbers of males and females. Error bars indicate standard deviation of the mean. For FIG. 1A, except for week 9 (p-value=0.2) and 10 (p-value=0.4), the p-value for each week was <0.003. For FIG. 1B, no significant differences were observed except for week 6 (p-value=0.02).

It has now been found that inhibition of ACAT1 is of use in the treatment of NPC disease, a disease where there is great need for effective therapies. NPC disease has no cure and children affected by the disease rarely live beyond 20 years of age. It is well-established that transport of cholesterol from endosomes/lysosomes to various cellular destinations requires NPC1 and NPC2 protein activity. Thus, decreased NPC1 or NPC2 activity, or a lack of activity, considerably slows the transport rate of cholesterol from endosomes/lysosomes to the ER for esterification. However, the NPC1/NPC2-dependent transport is not the only method for cholesterol trafficking in cells; there are other ways to deliver cholesterol to the ER for esterification such as through ACAT1 (as reviewed in Chang et al. 2006. *Ann. Rev. Cell Develop. Biol.* 22:129-157). In fact, in mutant NPC cells, the type of cells that are found in patients with NPC disease, although a large amount of unesterified cholesterol accumulates in membrane compartments, a significant amount of esterified cholesterol can still be found (Pentchev et al. 1986. *J. Biol. Chem.* 261:16775-16780). It has now been found that inhibiting ACAT1 can divert the cholesterol pool that would be used as ACAT1 substrate, such that this pool can be utilized by mutant NPC cells, thus partially sparing the need for cholesterol in these cells. Thus, inhibition of ACAT1 would lead to alterations in cholesterol trafficking in the cells and result in improvement in symptoms of NPC disease, such as accumulation of lipids that leads to progressive neurodegeneration, hepatomegaly and splenomegaly, and ultimately early death.

Having demonstrated that Acat1 gene ablation prolonged the lifespan of the Npc1$^{m/m}$ mouse by 34%, the present invention provides the first evidence that ACAT1 inhibitors would be useful as treatment for NPC disease and for prolonging survival in patients with NPC disease. In this respect, the present invention is a method for treating NPC disease in humans by administering to a patient diagnosed with NPC disease an effective amount of an ACAT1 inhibitor in a pharmaceutically acceptable vehicle. In accordance with the methods of this invention, a subject or patient, suspected of having or diagnosed with NPC is administered an effective amount of an agent that inhibits the activity of ACAT1 so that the signs and/or symptoms of NPC are decreased, delayed, or prevented thereby treating NPC.

In some embodiments, the ACAT1 inhibitor inhibits, to a certain degree, ACAT2. In this respect, the ACAT1 inhibitor is a non-selective ACAT inhibitor that is capable of inhibiting both ACAT1 and ACAT2. Inhibitors that inhibit both isoforms of ACAT include, for example, Avasimibe and Pactimibe. Avasimibe, also known as CI-1011, is an oral ACAT inhibitor that is non-selective as it inhibits both ACAT1 and ACAT2 activity with approximately equal potency (IC$_{50}$ of 18.7 µM and 19.1 µM, respectively; Ikenoya et al. 2007. *Atherosclerosis* 191:290). It has been shown to be safe when administered to rats, dogs, and humans (Llayerias et al. 2003. *Cardiovasc. Drug Rev.* 21:33-50). In vitro studies in human macrophages have demonstrated that Avasimibe reduces foam cell formation in macrophages by enhancing free cholesterol efflux and inhibiting the uptake of modified low-density lipoprotein (LDL; Rodriguez and Usher. 2002. *Atherosclerosis* 161:45-54). Studies in animal models have suggested that Avasimibe treatment could contribute to increase plaque stability in atherosclerosis (as reviewed in Llayerías et al. 2003. *Cardiovasc. Drug Rev.* 21:33-50). In clinical studies in humans, Avasimibe has been administered in combination with a statin drug, but failed to demonstrate efficacy to inhibit progression of coronary atherosclerosis in patients (Nissen et al. 2006. *NEJM* 354:1253-1263). Avasimibe also has been tested for efficacy to treat Alzheimer's disease (Huttunen et al. 2009. *FASEB J.* 23:3819-3828). Administering Avasimibe to a mouse model for Alzheimer disease led to significant decreases in amyloid plaque load and a reduction in cognitive deficits normally manifested in these animals (Huttunen et al. 2009. *FASEB J.* 23:3819-3828), indicating that CI-1011 could cross the blood brain barrier and enter the brain. Pactimibe is from the same drug class as Avasimibe (Terasaka et al. 2007. *Atherosclerosis* 190:239-247). Like Avasimibe, Pactimibe also inhibits both ACAT1 and ACAT2 with approximately equal potency (Kitayama et al. 2006. *Eur. J. Pharmacol.* 540:121-130), and has been administered to humans in clinical trials. Pactimibe also lacked efficacy as a supplement to statin treatment in patients with familial hypercholesterolemia (Meuwese et al. 2009. *JAMA* 301:1131-1139). Unlike Avasimibe, Pactimibe contains a carboxylate moiety, which may hinder its ability to cross the blood-brain barrier, making it ineffective as an oral treatment for diseases of the brain (e.g., Alzheimer's disease).

Additional non-selective ACAT inhibitors of use in the instant method include, but are not limited to CP-113,818 (Gutter-Paier et al. 2004. *Neuron* 44:227-238) and Ci-976 (Chang et al. 2000. *J. Biol. Chem.* 275:28083-28092).

In other embodiments of the present invention, the inhibitor is a selective inhibitor of ACAT1. As used herein, a "selective inhibitor of ACAT1" or "ACAT1-selective inhibitor" is any molecular species that is an inhibitor of the ACAT1 enzyme but which fails to inhibit, or inhibits to a substantially lesser degree ACAT2. Methods for assessing the selectively of ACAT1 inhibitors are known in the art and can be based upon any conventional assay including, but not limited to the determination of the half maximal (50%) inhibitory concentration (IC) of a substance (i.e., 50% IC, or $IC_{50}$), the binding affinity of the inhibitor (i.e., $K_i$), and/or the half maximal effective concentration ($EC_{50}$) of the inhibitor for ACAT1 as compared to ACAT2. See, e.g., Lada, et al. (2004) *J. Lipid Res.* 45:378-386 and U.S. Pat. No. 5,968,749. ACAT1 and ACAT2 proteins that can be employed in such assays are well-known in the art and set forth, e.g., in GENBANK Accession Nos. NP_000010 (human ACAT1) and NP_005882 (human ACAT2). See also U.S. Pat. No. 5,834,283.

In particular embodiments, a selective inhibitor of ACAT1 is an agent which has an $IC_{50}$ value for ACAT1 that is at least twice or, more desirably, at least three, four, five, or six times higher than the corresponding $IC_{50}$ value for ACAT2. Most desirably, a selective inhibitor of ACAT1 has an $IC_{50}$ value for ACAT1 which is at least one order of magnitude or at least two orders of magnitude higher than the $IC_{50}$ value for ACAT2.

Selective inhibitors of ACAT1 activity have been described. For example, Ikenoya et al. (2007. *Atherosclerosis* 191:290-297) teach that K-604 has an $IC_{50}$ value of 0.45 μmol/L for human ACAT1 and 102.85 μmol/L for human ACAT2. As such K-604 is 229-fold more selective for ACAT1 than ACAT2. K604 has been used in vivo in laboratory animals and has been shown to be safe for use in vivo (Ikenoya et al. 2007. supra). In addition, diethyl pyrocarbonate has been shown to inhibit ACAT1 with 4-fold greater activity ($IC_{50}$=44 μM) compared to ACAT-2 ($IC_{50}$=170 μM) (Cho et al. 2003. *Biochem. Biophys. Res. Comm.* 309:864-872). Ohshiro et al. (2007. *J. Antibiotics* 60:43-51) teach selective inhibition of beauveriolides I (0.6 μM vs. 20 μM) and III (0.9 μM vs. >20 μM) for ACAT1 over ACAT2. In addition, beauveriolide analogues 258, 280, 274, 285, and 301 show ACAT1-selective inhibition with $pIC_{50}$ values in the range of 6 to 7 (Tomoda & Doi. 2008. *Accounts Chem. Res.* 41:32-39). Lada, et al. (2004. *J. Lipid Res.* 45:378-386) teach a Warner-Lambert compound (designated therein as Compound 1A), and derivatives thereof (designated Compounds 1B, 1C, and 1D), which inhibit ACAT1 more efficiently than ACAT2 with $IC_{50}$ values 66- to 187-fold lower for ACAT1 than for ACAT2. Moreover, Lee et al. 2004. *Bioorg. Med. Chem. Lett.* 14:3109-3112) teach methanol extracts of *Saururus chinensis* root that contain saucerneol B and manassantin B for inhibiting ACAT activity. Saucerneol B inhibited hACAT-1 and hACAT-2 with $IC_{50}$ values of 43.0 and 124.0 μM, respectively, whereas manassantin B inhibited hACAT-1 and hACAT-2 with $IC_{50}$ values of 82.0 μM and only 32% inhibition at 1 mM, respectively.

Desirably, ACAT inhibitors of the present invention have an $IC_{50}$ value in the range of 1 nM to 100 μM. More desirably, ACAT inhibitors of the invention have an $IC_{50}$ value less than 100 μM, 50 μM, 10 μM, or 1 μM. Most desirably, ACAT inhibitors of the invention have an $IC_{50}$ value in the nM range (e.g., 1 to 999 nM).

In addition to the above-referenced ACAT inhibitors, it is contemplated that any conventional drug screening assay can be employed for identifying or selecting additional or more selective ACAT1 inhibitors or derivatives or analogs of known ACAT1 inhibitors. See, e.g., Lada et al. 2004. *J. Lipid Res.* 45:378-386. Such agents can be identified and obtained from libraries of compounds containing pure agents or collections of agent mixtures. Examples of pure agents include, but are not limited to, proteins, peptides, nucleic acids, oligonucleotides, carbohydrates, lipids, synthetic or semi-synthetic chemicals, and purified natural products. Examples of agent mixtures include, but are not limited to, extracts of prokaryotic or eukaryotic cells and tissues, as well as fermentation broths and cell or tissue culture supernates. In the case of agent mixtures, one may not only identify those crude mixtures that possess the desired activity, but also monitor purification of the active component from the mixture for characterization and development as a therapeutic drug. In particular, the mixture so identified may be sequentially fractionated by methods commonly known to those skilled in the art which may include, but are not limited to, precipitation, centrifugation, filtration, ultrafiltration, selective digestion, extraction, chromatography, electrophoresis or complex formation. Each resulting subfraction may be assayed for the desired activity using the original assay until a pure, biologically active agent is obtained.

Library screening can be performed in any format that allows rapid preparation and processing of multiple reactions such as in, for example, multi-well plates of the 96-well variety. Stock solutions of the agents as well as assay components are prepared manually and all subsequent pipetting, diluting, mixing, washing, incubating, sample readout and data collecting is done using commercially available robotic pipetting equipment, automated work stations, and analytical instruments for detecting the signal generated by the assay. Examples of such detectors include, but are not limited to, luminometers, spectrophotometers, calorimeters, and fluorimeters, and devices that measure the decay of radioisotopes. It is contemplated that any suitable ACAT enzymatic assay can be used in such screening assays.

As disclosed herein, there are a number of suitable molecules that selectively inhibit the activity of ACAT without modulating the expression of ACAT. However, in particular embodiments of the invention, an "ACAT inhibitor" inhibits the expression of ACAT1 and/or ACAT2 protein. Molecules that can inhibit ACAT expression include, e.g., siRNA, antisense molecules, or ribozymes. In particular embodiment, the ACAT inhibitor selectively inhibits the expression of ACAT1, without modulating the expression of ACAT2. While some RNAi molecules have been shown to induce significant neurotoxicity in brain tissue (McBride, et al. (2008) *Proc. Natl. Acad. Sci. USA* 105:5868-5873), specific embodiments of this invention embrace one or more siRNA or microRNA molecules as the ACAT1-selective inhibitor. As is conventional in the art, miRNA or microRNA refer to 19-25 nucleotide non-coding RNAs derived from endogenous genes that act as post-transcriptional regulators of gene expression. They are processed from longer (ca 70-80 nucleotide) hairpin-like precursors termed pre-miRNAs by the RNAse III enzyme Dicer. MicroRNAs assemble in ribonucleoprotein complexes termed miRNPs and recognize their target sites by antisense complementarity thereby mediating down-regulation of their target genes. By way of illustration, target sequences for mouse ACAT1 microRNA molecules include, but are not limited to, those listed in Table 1.

TABLE 1

| microRNA | ACAT1 Target Sequence | SEQ ID NO: |
|---|---|---|
| #52 | GGAGCTGAAGCCACTATTTAT | 1 |
| #53 | CTGTTTGAAGTGGACCACATCA | 2 |
| #54 | CCCGGTTCATTCTGATACTGGA | 3 |
| #55 | AACTACCCAAGGACTCCTACTGTA | 4 |

For example, pre-microRNAs (including sense, antisense and loop regions) that target microRNAs #54 and #55 were generated and shown to decrease mouse ACAT1 expression. These pre-microRNAs included 5'-TGC TGT CCA GTA TCA GAA TGA ACC GGG TTT TGG CCA CTG ACT GAC CCG GTT CAC TGA TAC TGG A-3' (SEQ ID NO:5) and 5'-TGC TGT ACA GTA GGA GTC CTT GGG TAG TTT TGG CCA CTG ACT GAC TAC CCA AGC TCC TAC TGT A-3' (SEQ ID NO:6).

Artificial microRNAs against human ACAT1 gene (e.g., GENBANK Accession No. NM_000019) were also generated and shown to decrease human ACAT1 protein expression by 80% in human cells. Exemplary microRNA sequences targeting human ACAT1 include, but are not limited, those listed in Table 2.

TABLE 2

| MicroRNA Sequence (5'->3') | SEQ ID NO: |
|---|---|
| CAUGAUCUUCCAGAUUGGAGUUCUA | 7 |
| UAGAACUCCAAUCUGGAAGAUCAUG | 8 |

In a similar manner, microRNA against the ACAT1 gene in primates (e.g., GENBANK Accession No. XM_508738, incorporated by reference) can be developed, and used to selectively inhibit the expression of primate ACAT1.

SiRNA or microRNA molecules which selectively inhibit the expression of ACAT1 or ACAT2 can be administered as naked molecules or via vectors (e.g., a plasmid or viral vector such as an adenoviral, lentiviral, retroviral, adeno-associated viral vector or the like) harboring nucleic acids encoding the siRNA or microRNA. Desirably, a vector used in accordance with the invention provides all the necessary control sequences to facilitate expression of the siRNA or microRNA. Such expression control sequences can include but are not limited to promoter sequences, enhancer sequences, etc. Such expression control sequences, vectors and the like are well-known and routinely employed by those skilled in the art. In particular embodiments, the siRNA or microRNA is delivered by a non-viral delivery method, e.g., liposome, nanoparticle, or liposome-siRNA-peptide complex (Pulford et al. 2010. *PloS One* 5:e11085.

Routine experimentation can be performed to demonstrate the efficacy of ACAT inhibitors in NPC disease. The first step is to examine the pharmacokinetics of an ACAT inhibitor, specifically its ability to distribute into the central nervous system as well as peripheral tissues when administered systemically, the preferred route of administration for a human drug product. In the context of the present invention, systemic administration includes administration orally, subcutaneously, by intravenous injection, rectally, topically, or by inhalation. Next, the efficacy of an ACAT inhibitor is demonstrated first in an animal model of NPC disease, and then in clinical studies. Progressing through each of these steps is the routine method used when developing a human drug.

When used in the methods of this invention, one or more ACAT inhibitors are administered to a subject in need of treatment in an amount that effectively reduces the expression or activity of ACAT by at least 60%, 70%, 80%, 90%, 95%, 99% or 100%. Subjects benefiting from treatment with an inhibitor of the invention include subjects confirmed as having NPC, subjects suspected of having NPC, or subjects at predisposed to have NPC (e.g., subjects with a family history of NPC disease). In the context of this invention, a subject can be any mammal including human, companion animals (e.g., dogs or cats), livestock (e.g., cows, sheep, pigs, or horses), or zoological animals (e.g., monkeys). In particular embodiments, the subject is a human.

While certain embodiments of this invention embrace in vivo applications, in vitro use of inhibitors of the invention are also contemplated for examining the effects of ACAT inhibition on particular cells, tissues or organs.

When used in therapeutic applications, an ACAT inhibitor of the invention will have the therapeutic benefit of decreasing, reducing or ameliorating one or more signs or symptoms of NPC disease including, but not limited to, enlargement of the spleen (splenomegaly), enlargement of the liver (hepatomegaly), jaundice, or weight loss, or neurological decline in the subject as compared to subjects not receiving treatment with the ACAT inhibitor and/or prolonging the lifespan of patients with NPC disease as compared to subjects not receiving treatment with the ACAT1 inhibitor. Based upon a decrease in signs and symptoms of NPC disease, it is expected that the subject receiving treatment will exhibit a delay or treatment of the NPC disease.

For therapeutic use, ACAT inhibitors can be formulated with a pharmaceutically acceptable carrier at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically acceptable carrier, composition or vehicle, such as a liquid or solid filler, diluent, excipient, or solvent encapsulating material, is involved in carrying or transporting the subject agent from one organ, or portion of the body, to another organ, or portion of the body. Each carrier must be acceptable in the sense of being compatible with the other ingredients of the formulation and not injurious to the patient.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Compositions of the present invention can be administered parenterally (for example, by intravenous, intraperitoneal, subcutaneous or intramuscular injection), topically, orally, intranasally, intravaginally, or rectally, or by central nervous system administration, such as intracerebroventricular injections into the left ventricle, according to standard medical practices.

The selected dosage level of an ACAT inhibitor will depend upon a variety of factors including the activity of the particular agent of the present invention employed, the route of administration, the time of administration, the rate of excretion or metabolism of the particular agent being employed, the duration of the treatment, other drugs, compounds and/or materials used in combination with the particular agent employed, the age, sex, weight, condition, general health and prior medical history of the patient being treated, and other factors well-known in the medical arts.

A physician having ordinary skill in the art can readily determine and prescribe the effective amount of the pharmaceutical composition required based upon the administration of similar compounds or experimental determination. For example, the physician could start doses of an agent at levels lower than that required in order to achieve the desired therapeutic effect and gradually increase the dosage until the desired effect is achieved. This is considered to be within the skill of the artisan and one can review the existing literature on a specific agent or similar agents to determine optimal dosing.

By way of illustration, administration of Avasimibe at a dose of 14.4 mg/kg/day has been shown to provide beneficial activity in a mouse model for Alzheimer's disease (Huttunen et al. 2009. *FASEB J.* 23:3819-3838). Because Alzheimer's disease is closely associated with accumulation of plaques and tangles in the central nervous system (CNS), it can be assumed that Avasimibe entered the CNS in vivo, although drug content in the treated mouse brain tissue was not reported. To demonstrate efficacy via a mouse model of NPC disease, Avasimibe is administered on a daily basis at different doses and the pharmacokinetics and pharmacodynamics of the drug are monitored in the mouse model of NPC disease.

The following non-limiting examples are provided to further illustrate the present invention.

EXAMPLE 1

ACAT1-Deficiency Prolongs Survival of NPC$^{m/m}$ Mice

The Npc1$^{m/m}$ mouse model was chosen for use as the NPC disease model. Experiments were conducted in both male and female mice bred specifically to express the desired traits by crossing Acat1$^{-/-}$ mice with Npc1$^{m/m}$ mice to generate a mouse model that was ACAT1-deficient and also exhibiting the NPC disease phenotype. The mice were observed for the effect of Acat1 gene ablation (ACAT1 inhibition) on lifespan and on symptoms associated with the NPC disease phenotype. The results showed that Acat1 gene ablation prolonged the lifespan of the Npc1$^{m/m}$ mouse by 34% (Npc1$^{m/m}$, Acat1$^{-/-}$) as compared to Npc1$^{m/m}$ mice without Acat1 gene knockout (Npc1$^{m/m}$, Acat1$^{+/+}$). Specifically, median survival for Npc1$^{m/m}$, Acat1$^{+/+}$ mice (N=13) was 113 days while in Acat1$^{-/-}$ mice (N=7) median survival was 138 days; and mean survival in the Npc1$^{m/m}$, Acat1$^{+/+}$ mice was 102 days while in Npc1$^{m/m}$, Acat1$^{-/-}$ mice mean survival was 137 days (P=2.39 E-6). Comparable numbers of male and female mice were used in this analysis.

Figure 1B:
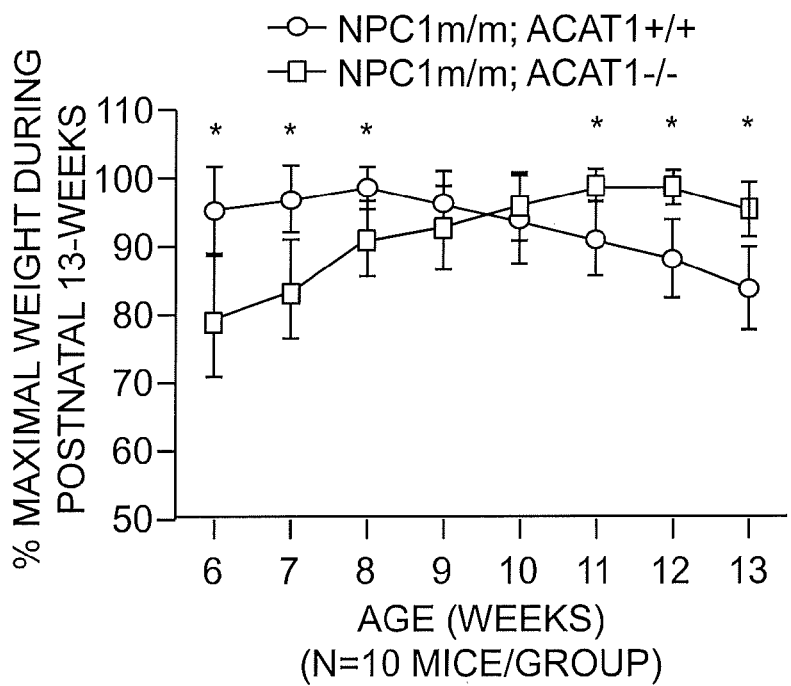

In addition, the onset of weight loss typically observed in the NPC disease mouse model was significantly delayed (FIG. 1). Histological examination of tissues removed from all mice at death showed that the Npc1$^{m/m}$, Acat1$^{-/-}$ mice (NPC disease phenotype with no ACAT1 activity) exhibited improved foam cell pathology in spleen but not in lung, as well as exhibiting significant delays in Purkinje neuronal cell loss in the cerebellum without affecting Purkinje neuron number in wild-type (NPC1$^{+/+}$) mice at PND 80, all characteristic lesions seen in the NPC disease model. Thus, these results provided evidence that inhibition of ACAT1 activity in NPC disease would be a useful strategy for drug development in order to prolong survival in patients with NPC disease.

EXAMPLE 2

Efficacy of ACAT Inhibitors in the Treatment of NPC Disease

Experiments are performed in a mouse model of NPC disease, Npc1$^{m/m}$ wild-type mice. Based on earlier work showing that drug treatment is effective in prolonging the lifespan of the NPC$^{-/-}$ mice only when mice were treated at a very young age (PND 7) (Liu et al. 2010. *J. Lipid Res.* 51:933-944; Griffin et al. 2004. *Nat. Med.* 10:704-711; Liu et al. 2009. *Proc. Natl. Acad. Sci. USA* 106:2377-2382), experiments are carried out by beginning treatment of mice on PND 7 (preweaning) or PND 21 (the day when mice are weaned). For mice at PND 7, the ACAT inhibitor (e.g., CI-1011) is administered in sesame oil by daily subcutaneous injection for up to 7 days. The injection sites of all animals are uniform to ensure uniform delivery of drug to different tissues. For mice treated on PND 21, the ACAT inhibitor is suspended in methylcellulose and administered by oral gavage daily for up to 7 days. After each treatment, the ACAT inhibitor content in brain, liver, and plasma of treated mice is determined. Tissue and plasma sample analysis are performed using solid-phase extraction of the ACAT inhibitor followed by separation and quantification using high-pressure liquid chromatography with ultraviolet detector (see, e.g., Robertson et al. 2001. *Toxicol. Sci.* 59:324-334); the limit of detection is expected to be between 0.08 μg/ml and 0.25 μg/ml.

Experiments can also be performed in wild-type Npc1$^{m/m}$ mice to examine the efficacy of ACAT inhibitor to alter cholesterol trafficking. Specifically, the ability of the ACAT inhibitor to inhibit synthesis of labeled cholesteryl esters from labeled cholesterol in the mouse brain in vivo is monitored. The procedure involves injecting labeled cholesterol directly into the lateral ventricles of the mouse brain and measuring the formation of labeled cholesteryl esters three hours after injection. A similar procedure can be used to monitor the ability of the ACAT inhibitor to inhibit cholesterol ester biosynthesis in mouse liver.

Experiments can also be performed in Acat1$^{-/-}$ mice in order to establish control levels of activity for comparison of the ability of the ACAT inhibitor to affect cholesterol ester synthesis. Thus, efficacy of the ACAT inhibitor can be established by comparing results obtained using ACAT inhibitor treatment or the vehicle treatment only in wild-type Npc1$^{m/m}$ mice as compared to vehicle treatment only in Acat1$^{-/-}$ mice.

Beginning at PND 7 and continuing for 14 consecutive days (i.e., just before weaning), the effects of daily injections of ACAT inhibitor to young Npc1$^{m/m}$ mice is examined. The doses tested are levels that will result in identification of the maximal effective inhibitor concentration in the brain. At the end of the experiment, the effects of the ACAT inhibitor are determined by monitoring intra-neuronal cholesterol accumulation, ganglioside cholesterol accumulation, 24S-hydroxycholesterol content in the brain, and cholesteryl ester biosynthesis in the brains of Npc1$^{m/m}$ mice. For controls, the same analyses in Npc1$^{m/m}$/Acat1$^{+/+}$ mice and Npc1$^{m/m}$/Acat1$^{-/-}$ mice is performed using vehicle only. Comparison of results obtained in these three experimental groups is used to determine the short-term efficacy of the ACAT inhibitor.

Subsequently, experiments can be performed beginning at PND 21 and continuing for 4 to 5 months (i.e., for the remaining lifespan of the mice). The animals are bred and weaned, and then treated with the ACAT inhibitor by oral gavage once per day, or by using implanted osmotic minipump (Alzet 1004), at the level determined to be the maximal effective concentration. Half of these mice are ones without prior exposure to the ACAT inhibitor before weaning; the other half will have been treated with daily injection of the inhibitor starting at PND 7 for 14 days. At PND 80, the effects of the ACAT inhibitor on intraneuronal cholesterol accumulation, ganglioside accumulation, and 24S-hydroxycholesterol levels in the brains of the Npc1$^{m/m}$ mice are again determined. In addition, the effects of the ACAT inhibitor on foam cell formation in the liver, spleen, and lung is examined, as well as Purkinje neuron retention in the brain, motor skill retention, weight loss, and lifespan. For controls, the same analyses are performed using npc1$^{m/m}$/Acat1$^{+/+}$ mice and Npc1$^{m/m}$/Acat1$^{-/-}$ mice treated with vehicle only. Comparison of results obtained in these four experimental groups defines the long-term efficacy of the ACAT inhibitor as a treatment for NPC disease.

The results of these experiments provide the basis for use of ACAT1 inhibitors as treatment for NPC disease in humans. As will be understood by one of skill in the art, results of drug testing in preclinical models of disease are routinely used to set doses for testing in humans. In conjunction with the information of toxicity observed in the NPC disease mouse model, doses for testing in humans can be determined by one of skill in the art. It is anticipated that the method of the present invention could involve administration of an ACAT1 inhibitor either alone or in combination with other drugs known to have efficacy in treating symptoms of PNC disease (i.e., miglustat). The ACAT1 inhibitor can be administered to a patient suffering from NPC disease in a pharmaceutically acceptable vehicle by any desired route.

EXAMPLE 3

Determination of Sterol Composition Analysis in Mouse Brains

Mice forebrains are homogenized and extracted using chloroform:methanol (2:1; at 12 mL final volume per mouse brain), dried down under nitrogen, and redissolved in MeOH. A 10% sample is placed in a 2-mL GC/MS autosampler vial, dried down, and trimethyl-silyl derivatized overnight at room temperature with 0.5 mL TRI-SIL TBT (Pierce). One microliter of derivatized sample (or 0.1 µL for cholesterol measurements) is injected into a SHIMADZU QP 2010 GC-MS instrument. GC/MS analysis of sterols is according to known methods (see Ebner et al. 2006. *Endocrinology* 147:179-190) using selected ion monitoring (cholesterol, 329, 353, 368, 458; desmosterol, 441; lanosterol, 393; 24SOH, 413) and standard curves for quantification.

EXAMPLE 4

Determination of Ganglioside Accumulation

Lipids are extracted as described above. Gangliosides are separated from other lipids on a 1 g silica gel column (Silica gel 60, 230-400 mesh, Merck A. G., Darmstadt, FRG) packed in chloroform (Svennerholm et al. 1991. *J. Neurochem.* 56:2051-2059). The lipid sample is redissolved in 2 ml of chloroform-methanol (9:1, v/v), applied to the column, the flask rinsed and applied to the column with two portions of 1 ml of the same solvent. The flask is finally rinsed with 2 ml of chloroform-methanol-water (65:25:4, v/v/v) which is also added to the column. Finally, the column is eluted with additional 6 ml of chloroform-methanol-water (65:25:4, v/v/v). All the eluates to this point are pooled and designated as the 'non-ganglioside lipid fraction'. Then the 'ganglioside fraction' is eluted with additional 10 ml of chloroform-methanol-water (3:6:2, v/v/v). Test runs and thin-layer chromatography are used to demonstrate that all non-ganglioside lipids including sphingomyelin are in the first fraction and all gangliosides including GM3 are in the ganglioside fraction without cross-contamination.

EXAMPLE 5

Determination of Foam Cell Formation in Organs

Cells on slides are washed in distilled water, rinsed in 60% isopropanol, and stained with 0.2% Oil Red O (Sigma) for 15 minutes. Slides are rinsed again with 60% isopropanol and dipped in hematoxylin to stain for cell nuclei. After washing with distilled water, coverslips are mounted on slides. Foam cells, recognized as macrophages stained with Oil Red O, are visualized via light microscope (Olympus 820) with 100× magnification. Foam cells, as well as the total cell number/well on each slide, are quantitated manually, and the percentage of foam cells present is calculated as the number of foam cells present divided by the total number of cells in each well.

EXAMPLE 6

Motor Skill Assessment

Motor skills of the NPC disease animal model can be assessed by monitoring behavioral attributes such as crossing (forward movements of the body); immobility (no visible movements of the body); head moving (head raising and head turning); wall climbing; pivoting (turning to left or right propelled only by forelimbs; hind limbs stationary); and/or grooming (signs of wiping).

Alternatively, or in addition to, mouse motor skills are monitored by subjecting mice to three consecutive trials each week to a constant speed (24 rpm) rotor rod for up to 90 seconds per each trial. Fail time is recorded as the age at which the mouse failed to stay on the rotor-rod for at least 10 seconds during one of the three trials, or by freezing on the rotor-rod and not moving. Rotor rod methods are known in the art and described in Bascunan-Castillo et al. 2004. *J. Appl. Genet.* 45:461 and Kim et al. 2008 *Proc. Natl. Acad. Sci. USA* 105:2094-2099.

EXAMPLE 7 siRNA Inhibition of ACAT1

Four different siRNA sequences (#52-#55) targeting the mouse Acat1 (also called Soat1) gene were inserted into an endogenous mouse microRNA (miR) scaffold using Invitrogen's RNAi design tool. The artificial miRs were ligated into the mammalian expression vector pcDNA6.2-GW/EmGFP-miR. These Acat1miR constructs were tested along with a negative control (NC) miR (5'-TACTGCGCGTGGAGACG-3'; SEQ ID NO:9), which does not match the sequence of any known vertebrate gene, in NIH-3T3 mouse fibroblasts. The miRs were delivered to the cells by using standard cDNA transfection protocol. The results show that two of the Acat1 miRs (containing the siRNA sequence #54, 5'-TACAGTAG-GAGTCCTTGGGTA-3', SEQ ID NO:10; and sequence #55, 5'-TCCAGTATCAGAATGAACCGGG-3', SEQ ID NO:11) were effective in causing a 50-60% reduction in the ACAT1 protein content in treated mouse 3T3 fibroblasts. These two Acat1 miR sequences and the NC miR sequence were also subcloned into an rAAV backbone vector (AAV-6P-SEWB) that contained the neuron-specific hSyn promoter. This vector contains a strong and cell-type-nonspecific promoter that expresses Acat1 miRs in any cell type where the viral genome is expressed. For identification purpose, it also coexpresses the GFP with the miRs. These three constructs were used to produce three recombinant AAV viruses. To test the efficacy and specificity of these viruses, cultured primary hippocampal neurons were treated with the NC AAV, or with AAV that expresses miR that contain siRNA Acat1 #55. Two weeks after viral infection, the effects of AAVs on cholesteryl ester biosynthesis in neurons were tested. The results showed that the AAV harboring siRNA Acat1 #55 reduced cholesteryl ester biosynthesis by more than 50%, when compared with values in NC virus treated cells. Subsequently, the NC AAV or the Acat1 AAV (that include both siRNA Acat1 #54 and #55) were injected into the hippocampal region of mice at 4 month of age. After a single bilateral injection, mice were allowed to recover. One month after injection, mice were sacrificed and the ACAT1 enzyme activities in the mouse brain homogenates were analyzed by using standard ACAT enzyme activity assay in vitro. The result shows that when compared with the control values, the Acat1 AAV reduced ACAT1 enzyme activity by 42%.

What is claimed is:

1. A method for treating Niemann-Pick Type C disease comprising administering to a patient diagnosed with Niemann-Pick Type C disease an effective amount of an Acyl-CoA:Cholesterol Acyltransferase (ACAT) inhibitor in a pharmaceutically acceptable vehicle, wherein said ACAT inhibitor is a selective inhibitor of ACAT1 and further wherein said selective ACAT1 inhibitor is administered alone.

2. The method of claim 1, wherein the ACAT inhibitor has an $IC_{50}$ value for ACAT1 which is at least twice the corresponding $IC_{50}$ value for ACAT2.

3. The method of claim 1, wherein the selective inhibitor of ACAT1 is a microRNA.

4. The method of claim 2, wherein the ACAT1 inhibitor is administered via a liposome or nanoparticle.

5. The method of claim 1, wherein the ACAT inhibitor has an $IC_{50}$ value in the range of 1 nM to 100 μM.

* * * * *

```
                         SEQUENCE LISTING

<160> NUMBER OF SEQ ID NOS: 11

<210> SEQ ID NO 1
    <211> LENGTH: 21
    <212> TYPE: DNA
    <213> ORGANISM: Artificial Sequence
    <220> FEATURE:
    <223> OTHER INFORMATION: Synthetic oligonucleotide

<400> SEQUENCE: 1
ggagctgaag ccactattta t                                             21

<210> SEQ ID NO 2
    <211> LENGTH: 22
    <212> TYPE: DNA
    <213> ORGANISM: Artificial Sequence
    <220> FEATURE:
    <223> OTHER INFORMATION: Synthetic oligonucleotide

<400> SEQUENCE: 2
ctgtttgaag tggaccacat ca                                            22

<210> SEQ ID NO 3
    <211> LENGTH: 22
    <212> TYPE: DNA
    <213> ORGANISM: Artificial Sequence
    <220> FEATURE:
    <223> OTHER INFORMATION: Synthetic oligonucleotide

<400> SEQUENCE: 3
cccggttcat tctgatactg ga                                            22

<210> SEQ ID NO 4
    <211> LENGTH: 24
    <212> TYPE: DNA
    <213> ORGANISM: Artificial Sequence
    <220> FEATURE:
    <223> OTHER INFORMATION: Synthetic oligonucleotide

<400> SEQUENCE: 4
aactacccaa ggactcctac tgta                                          24

<210> SEQ ID NO 5
    <211> LENGTH: 64
    <212> TYPE: DNA
    <213> ORGANISM: Artificial Sequence
```

```
<220> FEATURE:
<223> OTHER INFORMATION: Synthetic oligonucleotide

<400> SEQUENCE: 5
tgctgtccag tatcagaatg aaccgggttt tggccactga ctgacccggt tcactgatac    60
tgga                                                                 64

<210> SEQ ID NO 6
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 6
tgctgtacag taggagtcct tgggtagttt tggccactga ctgactaccc aagctcctac    60
tgta                                                                 64

<210> SEQ ID NO 7
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 7
caugaucuuc cagauuggag uucua                                          25

<210> SEQ ID NO 8
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 8
uagaacucca aucuggaaga ucaug                                          25

<210> SEQ ID NO 9
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 9
tactgcgcgt ggagacg                                                   17

<210> SEQ ID NO 10
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 10
tacagtagga gtccttgggt a                                              21

<210> SEQ ID NO 11
<211> LENGTH: 22
<212> TYPE: DNA
<213> ORGANISM: Artificial sequence
```

```
<220> FEATURE:
<223> OTHER INFORMATION: Synthetic oligonucleotide

<400> SEQUENCE: 11
tccagtatca gaatgaaccg gg                                              22
```